United States Patent
Ju

(10) Patent No.: US 11,174,501 B2
(45) Date of Patent: Nov. 16, 2021

(54) ENZYME PROCESSING OF SOYBEANS INTO INTACT OIL BODIES, PROTEIN BODIES, AND HYDROLYZED CARBOHYDRATES

(71) Applicant: Lu-Kwang Ju, Akron, OH (US)

(72) Inventor: Lu-Kwang Ju, Akron, OH (US)

(73) Assignee: The University of Akron, Akron, OH (US)

( * ) Notice: Subject to any disclaimer, the term of this patent is extended or adjusted under 35 U.S.C. 154(b) by 106 days.

(21) Appl. No.: 16/715,617

(22) Filed: Dec. 16, 2019

(65) Prior Publication Data

US 2020/0190552 A1  Jun. 18, 2020

Related U.S. Application Data

(60) Provisional application No. 62/779,843, filed on Dec. 14, 2018.

(51) Int. Cl.
| | |
|---|---|
| C12P 19/14 | (2006.01) |
| C12P 21/00 | (2006.01) |
| C12P 7/64 | (2006.01) |
| C12P 19/02 | (2006.01) |

(52) U.S. Cl.
CPC .............. *C12P 21/00* (2013.01); *C12P 7/649* (2013.01); *C12P 19/02* (2013.01); *C12P 19/14* (2013.01)

(58) Field of Classification Search
CPC ............ C12P 21/00; C12P 19/14; C12P 7/649
See application file for complete search history.

(56) References Cited

U.S. PATENT DOCUMENTS

| | | | |
|---|---|---|---|
| 8,679,794 B2* | 3/2014 | Muniglia | C13B 20/002 435/99 |
| 9,809,630 B2 | 11/2017 | Ju et al. | |
| 2016/0304925 A1 | 10/2016 | Ju | |

OTHER PUBLICATIONS

Loman et al., Process Biochemistry, 68, 153-164, 2018.*

* cited by examiner

*Primary Examiner* — Maryam Monshipouri
(74) *Attorney, Agent, or Firm* — Renner Kenner Greive Bobak Taylor & Weber

(57) ABSTRACT

A method of enzyme-based processing of plant-based materials includes steps of providing a bulk amount of a plant-based material having a substantial amount of the cell walls in a physically-intact condition; providing an enzyme broth having an enzyme capable of breaking down the cell walls in the physically-intact condition; combining the bulk amount of the plant-based material with the enzyme broth; allowing the enzyme capable of breaking down the cell walls in the physically-intact condition to break down at least a portion of the cell walls in the physically-intact condition to thereby produce intact oil bodies, hydrolyzed carbohydrates, and intact protein bodies; collecting a first product including the intact oil bodies; collecting a second product including the hydrolyzed carbohydrates; and collecting a third product including the intact protein bodies.

14 Claims, 5 Drawing Sheets

ENZYME PROCESSING OF SOYBEANS INTO INTACT OIL BODIES, PROTEIN BODIES, AND HYDROLYZED CARBOHYDRATES

CROSS REFERENCE TO RELATED APPLICATIONS

This application claims the benefit of U.S. provisional patent application Ser. No. 62/779,843, filed Dec. 14, 2018, which is incorporated by reference herein in its entirety.

FIELD OF THE INVENTION

The present invention is directed to methods of enzyme-based processing for separating and collecting the major components of plant-based materials (e.g. soybeans) as intact oil bodies, intact protein bodies, and hydrolyzed carbohydrates.

BACKGROUND OF THE INVENTION

When processing plant-based materials, such as soybeans, it is desirable to recover as much nutritional and industrial value from the materials. However, as uses of these materials has evolved in different parts of the world, different processes have been developed, which tend to target producing particular products. As such, these diverse processes tend to leave the non-targeted components as widely different byproduct materials. Since the byproduct materials are quite different from process to process, recovery of useful components of these materials requires a particular process adapted to the particular byproduct material. Developing and optimizing these diverse and narrowly targeted methods can be difficult and expensive, and some of these byproduct materials are simply disposed as waste. Moreover, since the resulting products from these diverse methods will differ, there can be difficulty in establishing an end use. Thus, it would be desirable to have a processing method that unifies the product properties for more effective end use.

Certain existing methods for processing plant-based materials include extracting oil from the materials using hexane extraction. Hexane is derived from non-renewable petroleum sources and is highly flammable and explosive, posing hazards to personnel and properties. Moreover, the volatile hexane can react with nitrogen oxide to form ozone, causing health hazards for the surrounding community. Therefore, it would be desirable to have a processing method that does not require the use of hexane.

In addition to hexane extraction, other utilized pretreatment steps tend to destroy the cell structures of the plant-based materials. These steps will fragment and mix the subcellular components. Intact oil bodies can be utilized in high-value uses that involve stable oil-in-water systems, such as in food, cosmetic, and pharmaceutical applications. Use of oil bodies in these applications provides excellent stability of oil/water mixtures that otherwise may require the addition of high levels of synthetic surfactants. Further, these conventional pretreatment steps tend to make it difficult to separate protein from the indigestible carbohydrate in the plant meal after oil extraction. This can significantly decrease the value of collected protein and carbohydrate. Thus, there remains a need for a method that includes collecting intact oil bodies and separating protein and carbohydrate effectively.

Enzyme-assisted extractions have been utilized as an alternative to the hexane-based oil extraction. Enzymes have also been used for separating protein and carbohydrate. However, these methods tend to overly mix the various desired products in a way that does not allow maximal separation and recovery of the various product components. Moreover, these methods do not allow for the collection of intact oil bodies and protein bodies. Thus, there remains a need for a method that includes maximal separation of the various product components and collecting intact oil bodies and protein bodies.

SUMMARY OF THE INVENTION

Embodiments of the present invention provide a method of enzyme-based processing of plant-based materials, the method comprising steps of: providing a bulk amount of a plant-based material, the bulk amount of the plant-based material including a plurality of individual plant-based materials having cell walls, wherein the bulk amount of the plant-based material includes at least 90% of the cell walls in a physically-intact condition relative to a naturally-occurring amount of the cell walls in the physically-intact condition; providing an enzyme broth having an enzyme capable of breaking down the cell walls in the physically-intact condition; combining the bulk amount of the plant-based material with the enzyme broth; allowing the enzyme capable of breaking down the cell walls in the physically-intact condition to break down at least a portion of the cell walls in the physically-intact condition to thereby produce intact oil bodies, hydrolyzed carbohydrates, and intact protein bodies; collecting a first product stream including the intact oil bodies; collecting a second product stream including the hydrolyzed carbohydrates; and collecting a third product stream including the intact protein bodies.

BRIEF DESCRIPTION OF THE DRAWINGS

Advantages of the present invention will become better understood with regard to the following description, appended claims, and accompanying drawings wherein:

DETAILED DESCRIPTION OF THE ILLUSTRATIVE EMBODIMENTS

Embodiments of the present invention are directed to a method of enzyme-based processing of plant-based materials. The plant-based materials that are processed include a substantial amount of their cell walls in a physically-intact condition relative to a naturally-occurring amount of the cell walls in the physically-intact condition. That is, naturally-occurring plant-based materials (e.g. soybeans taken from a soybean plant) include an initial amount of physically-intact cell walls. Conventional processing of plant-based materials tends to utilize pretreatment steps that will physically break a significant amount of the cell wall structures of the plant-based materials. The present method retains the substantial amount of the cell walls in the physically-intact condition prior to combining the plant-based materials with an enzyme broth having an enzyme capable of breaking down the cell walls in the physically-intact condition. The enzyme broth and the enzyme therein then enzymatically break down the cell walls in the physically-intact condition to thereby produce separate products including intact oil bodies, hydrolyzed carbohydrates, and intact protein bodies. One or more advantages derived by the present method include: recovering and separating the major component groups of the plant-based materials, simplifying processing of plant-based materials, unifying the product properties for more effective subsequent uses and development, collecting the protein and oil of the plant-based materials as intact protein bodies and intact oil bodies, which may also be referred to as oleosomes or spherosomes, and enzymatically processing plant-based materials effectively without the protein and oil bodies and cell wall carbohydrates being significantly mixed, blended, pressed, and/or altered as in conventional plant-based materials processing.

Figure 1:
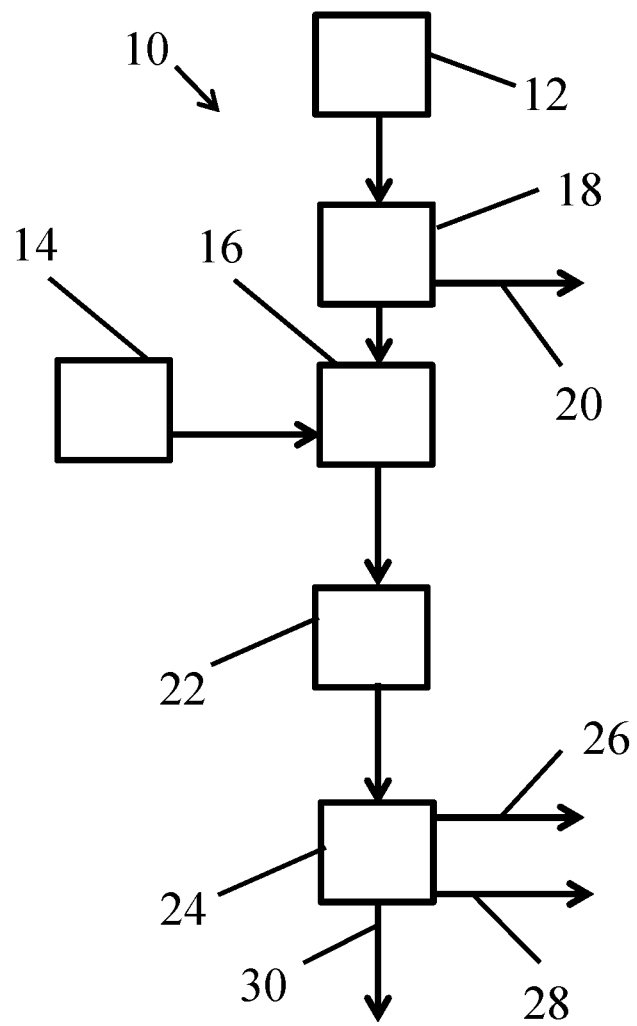
FIG. 1 is a schematic showing a process according to one or more embodiments of the present invention.
Figure 2:
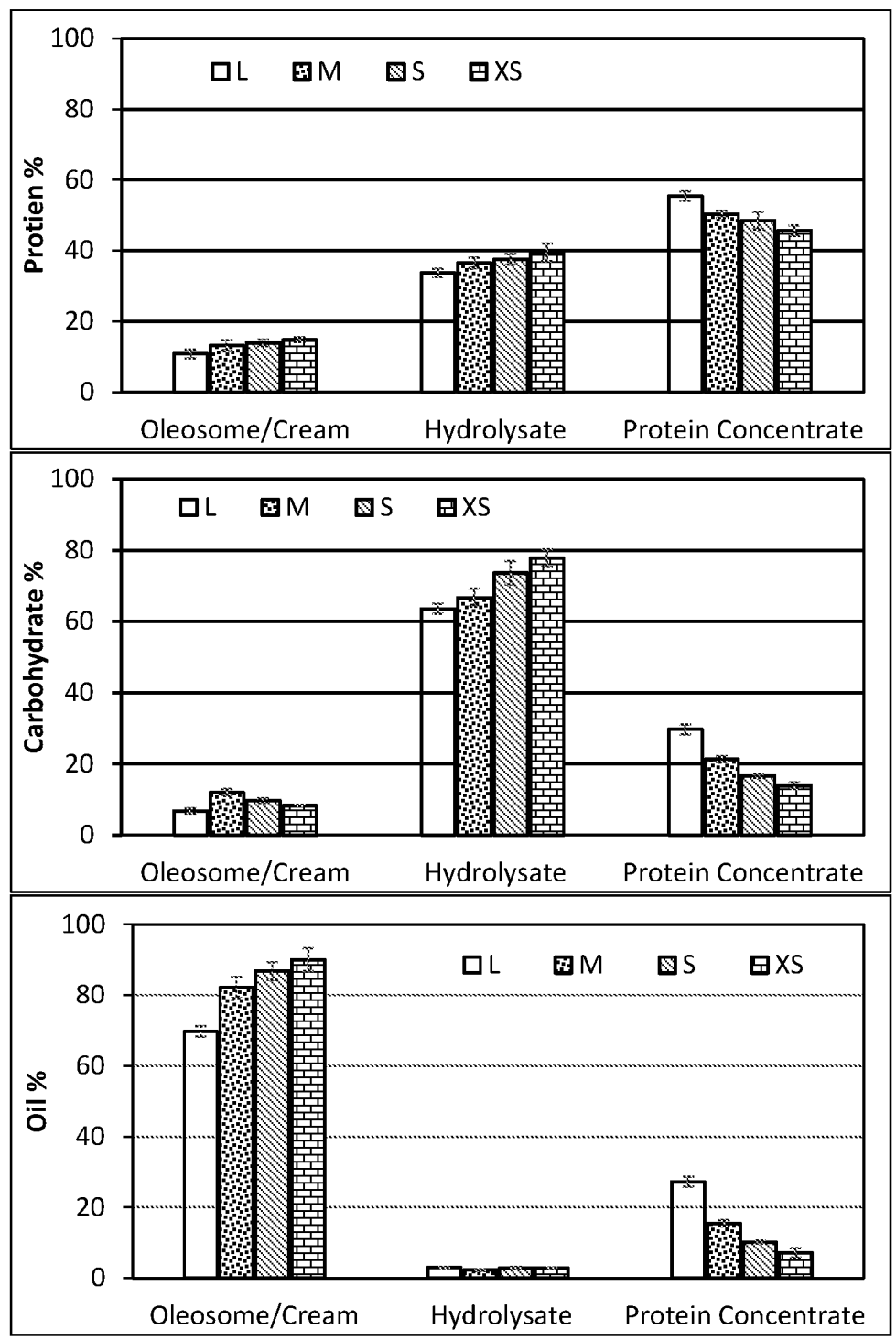
FIG. 2 is graphs showing the effect of particle size on oil extraction and protein-carbohydrate separation according to examples of one or more embodiments of the present invention.

Aspects of one or more embodiments of the present invention can be described with reference to FIG. 1, which shows a method 10 of enzyme-based processing of plant-based materials. A plant-based material 12, which may also be referred to as a bulk amount of plant-based material 12, is provided. Plant-based material 12 includes a plurality of individual plant-based materials (e.g. soybeans) having cell walls in a physically-intact condition. Bulk amount of plant-based material 12 includes a substantial amount of the cell walls in the physically-intact condition. The reference to the substantial amount is relative to the naturally-occurring amount of the cell walls in the physically-intact condition in the plant-based material.

An enzyme broth 14, which may also be referred to as an enzyme mixture 14, is provided. Enzyme broth 14 includes one or more enzymes capable of breaking down the cell walls in the physically-intact condition. Enzyme broth 14 may be obtained from suitable sources or may be produced by a fungal fermentation. Enzyme broth 14 is combined with plant-based material 12 in a combining step 16, which may be within any suitable vessel. In one or more embodiments, plant-based material 12 may be provided to combining step 16 in the original form of plant-based material 12 (e.g. without breaking plant-based material 12 into smaller pieces).

Prior to combining step 16, plant-based material 12 may optionally be subjected to a minor pretreating step 18. Minor pretreating step 18 may produce a byproduct 20. An exemplary minor pretreating step 18 is dehulling plant-based material 12 to remove the hulls (i.e. byproduct 20) thereof. Other exemplary minor pretreating step 18 include cracking and cutting. Minor pretreating step 18 may slightly break plant-based material 12 into smaller pieces. In doing so, minor pretreating step 18 may physically break a minor amount of the cell walls of plant-based material 12, but minor pretreating step 18, where utilized, retains a substantial amount of the cell walls of plant-based material 12 in the physically-intact condition.

After combining step 16, the combination of plant-based material 12 and enzyme broth 14 is allowed to undergo an enzymatic processing step 22. Enzymatic processing step 22 includes allowing enzyme broth 14 to enzymatically break down the cell walls of plant-based material 12 to produce product components of intact oil bodies, hydrolyzed carbohydrates, and intact protein bodies. Enzymatic processing step 22 may occur in the same vessel as combining step 16. In other embodiments, enzymatic processing step 22 may occur in a different vessel than combining step 16.

In one or more embodiments, the mixture within enzymatic processing step 22 may be subjected to sonication. The sonication may serve to improve oil extraction from plant-based materials 12, as well as improving the collection and separation of product components.

After enzymatic processing step 22, the resulting mixture may undergo a product separation step 24 to separate the product components. Product separation step 24 may include collecting three separate product streams. A first product stream 26 generally includes the intact oil bodies as a primary component. First product stream 26 may be in the form of cream or oleosomes. A second product stream 28, which may be referred to as a liquid hydrolysate 28, generally includes the hydrolyzed carbohydrates as a primary component. Second product stream 28 may be in liquid form. A third product stream 30, which may be referred to as a protein concentrate 30, generally includes the intact protein bodies as a primary component. Third product stream 30 may include other precipitated solids. Third product stream 30 may be in wet solid slurry or paste form, with the aqueous phase filling the interstitial space between solid precipitates (predominantly hydrated protein bodies). Product streams 26, 28, 30 may optionally undergo further processing (not shown) in order to prepare a more useful product. For example, third product stream 30 may be dried to obtain a final solid protein product.

An exemplary product separation step 24 is centrifugation. Product separation step 24 may occur in the same vessel as enzymatic processing step 22. In other embodiments, product separation step 24 may occur in a different vessel or device, such as a centrifuge, than enzymatic processing step 22.

The plant-based materials (i.e. plant-based materials 12), which may also be referred to as protein-rich materials, can include any plant seeds, fruit, or other biomass, and products made therefrom, with the provision that plant-based materials should include a substantial amount of their cell walls in a physically-intact condition relative to a naturally-occurring amount of the cell walls in the physically-intact condition, as discussed elsewhere herein. Exemplary plant-based materials include soybean, canola, sunflower, cottonseed, safflower, caster bean, peanut, cashew, almond, macadamia nut, hazelnut, cucumber seed, squash seed, zucchini seed, onion seed, cabbage seed, jojoba, pecan, flaxseed, pistachio, poppy seed, mustard, sesame seed, corn (or corn germ), oil palm, olive, avocado, coconut, and essentially all plant seeds and fruits that store oil (i.e., lipids, primarily triacylglycerols) as a form of energy. The plant-based materials generally include many cells, which are separated by cell walls. The cells include many protein bodies and oil bodies, and discussed herein, it is desirable to collect these protein bodies and oil bodies in an intact condition.

In one or more embodiments, plant-based materials can be characterized as having about 20% to about 60% protein, in other embodiments, about 30% to about 50% protein, and in other embodiments, about 35% to about 45% protein, and in other embodiments, about 40% protein.

In one or more embodiments, plant-based materials can be characterized as having about 5% to about 35% oil, in other embodiments, about 15% to about 25% oil, and in other embodiments, about 18% to about 20% oil.

In one or more embodiments, plant-based materials can be characterized as having about 10% to about 80% carbohydrate, in other embodiments, about 20% to about 35% carbohydrate, and in other embodiments, about 25% to about 30% carbohydrate.

With respect to soybeans as the plant-based materials, soybean hull carbohydrates are composed mainly of cellulose, hemicellulose, and pectin. As discussed elsewhere herein, these hulls may be removed by a dehulling step. In other embodiments, it may be desirable to collect the hull carbohydrates.

If dehulling occurs, after dehulling, cell walls in the cotyledons are the primary barrier to extraction of oil from the cells. The cell wall is constructed of pectin, hemicellulose, and microfibrils of cellulose crosslinked with pectin. Within the primary cell wall, there is a secondary cell wall of cellulose and hemicellulose. The cells are held together by a middle lamella composed of pectin. In intact cells, mass transfer across the cell wall barrier is believed to occur only through small openings, ranging from 20-80 nm in diameter.

A soybean generally includes four basic parts: a soybean hull (outside coat) (8%), the plumule and hypocotyl-axis (2%) and two large cotyledons (90%). The cotyledons include cylindrical cells (30 μm×70 μm) that are filled predominantly with protein and oil. Each cell has a protective cell wall structure that includes carbohydrates such as cellulose, hemicellulose, and pectin. Most of the protein is packaged as nearly spherical protein bodies of 2 to 10 μm in diameter. The oil is stored as much smaller (approximately 0.2 to 0.5 μm in diameter) particles, which may be referred to as oil bodies, oleosomes, or spherosomes. These small oil bodies fill the space between the protein bodies. The oil bodies are stabilized by a single phospholipid layer interspersed with amphipathic proteins oleosins. Oleosins are very important for stabilizing oil bodies in both cellular and aqueous environments.

As suggested above, the plant-based materials may be subjected to a minor pretreating step (i.e. minor pretreating step 18). The minor pretreating step may serve to provide an initial function, such as removing hulls. Where the minor pretreating step is utilized, the plant-based materials retain a substantial amount of the cell walls in the physically-intact condition. The presence or absence of the minor pretreating step may determine the most suitable enzyme composition of the enzyme broth.

As suggested above, a minor pretreating step may include removing hulls, which may also be referred to as a dehulling step. Suitable techniques and aspects of a dehulling step may be generally known to the skilled person. As suggested above, even if a dehulling step is utilized, the plant-based materials retain a substantial amount of the cell walls in the physically-intact condition.

As suggested above, a minor pretreating step may include slightly breaking plant-based material into smaller pieces, which may also be referred to as a cracking step. Suitable techniques and aspects of a cracking step may be generally known to the skilled person. A dehulling function and a cracking function may be accomplished by a single step or technique. As suggested above, even if a cracking step is utilized, the plant-based materials retain a substantial amount of the cell walls in the physically-intact condition.

As suggested above, a minor pretreating step may include sonicating the plant-based material, which may also be referred to as a sonication step. Suitable techniques and aspects of a sonication step may be generally known to the skilled person. As suggested above, even if a sonication step is utilized, the plant-based materials retain a substantial amount of the cell walls in the physically-intact condition.

Where utilized, sonication is believed to facilitate dislodging of protein bodies and oil bodies from any cells that have at least partially broken or hydrolyzed cell walls. These cells are generally believed to be in the outer layer of the plant-based materials. Dislodging these protein bodies and oil bodies from the outer layer may expose the underneath cell walls for easier enzyme access and attack in the subsequent enzyme processing step.

As suggested above, a minor pretreating step may include a slight mechanical method, such as mixing, for the plant-based material. Suitable techniques and aspects of a slight mechanical step may be generally known to the skilled person. As suggested above, even if a slight mixing step is utilized, the plant-based materials retain a substantial amount of the cell walls in the physically-intact condition. Slight mixing may serve to dislodge the protein bodies and oil bodies from the outer layer.

As suggested above, the plant-based materials may be provided in their original form without breaking into smaller pieces. This may be referred to as providing the plant-based materials enzymatic processing in their original particle size.

As suggested above, in other embodiments, the plant-based materials may be broken into smaller pieces before enzymatic processing. This may be referred to as adjusting the particle size of the plant-based material.

In one or more embodiments, the average particle size of the plant-based material is greater than 2.38 mm, in other embodiments, from about 2.38 mm to about 1.19 mm, in other embodiments, from about 1.19 mm to about 0.42 mm, and in other embodiments, less than 0.42 mm. In one or more embodiments, the average particle size of the plant-based material is less than 2.38 mm, and in other embodiments, less than 1.19 mm. In one or more embodiments, the average particle size of the plant-based material is greater than 1.19 mm, and in other embodiments, greater than 0.42 mm.

For those embodiments using relatively smaller particle sizes, efficiency of the enzymatic processing may be improved. This is believed to be based on the enzyme destroying the cell walls, and releasing the oil bodies and protein bodies, in an inward layer-by-layer manner. Smaller particles generally provide larger specific external surface areas for initial enzyme attack and have smaller radii/depths for the inward enzyme attack to penetrate.

As suggested above, the plant-based materials that are enzymatically processed include a substantial amount of their cell walls in a physically-intact condition relative to a naturally-occurring amount of the cell walls in the physically-intact condition. The amount of retained cell walls in a physically-intact condition may be quantified based on the initial amount of cell walls in a physically-intact condition in naturally-occurring plant-based materials.

In one or more embodiments, the plant-based materials that are enzymatically processed, which may be referred to as a bulk amount of the plant-based materials, include at least 90%, in other embodiments, at least 95%, in other embodiments, at least 98%, and in other embodiments, at least 99% of their cell walls in a physically-intact condition relative to the initial, naturally-occurring amount of the cell walls in the physically-intact condition.

In one or more embodiments, the plant-based materials that are enzymatically processed, which may be referred to as a bulk amount of the plant-based materials, include about 95%, in other embodiments, about 98%, in other embodiments, about 99%, and in other embodiments, about 100% of their cell walls in a physically-intact condition relative to the initial, naturally-occurring amount of the cell walls in the physically-intact condition.

These quantifications as to the amount of retained cell walls in a physically-intact condition may be generally determined based on surface area analysis. That is, given that an initial, naturally-occurring plant-based material has an initial or original surface area per unit weight, the analysis of quantifying an amount of the cell walls in the physically-intact condition of a subsequent condition of the plant-based material may be based on analyzing the surface area per unit weight of the subsequent plant-based material relative to the initial surface area per unit weight. It is believed that any increase in surface area per unit weight is based on the cell walls being physically broken. Suitable techniques for surface area analysis are generally known to the skilled person.

With respect to the cell walls in the physically-intact condition, the oligomeric and polymeric molecules making up the cell wall are not broken down. Within the enzymatic processing (i.e. enzymatic processing step 22) these oligomeric and polymeric molecules of the cell walls are hydrolyzed by the enzymes into monomers. This also reveals the intact protein bodies and oil bodies contained by the cell wall.

As suggested above, the amount of plant-based material may be referred to as a bulk amount. In one or more embodiments, a bulk amount of the plant-based materials may include at least 0.1 pounds, in other embodiments, at least 10 pounds, and in other embodiments, at least 1,000 pounds of the plant-based materials. In one or more embodiments, a bulk amount of the plant-based materials may include from about 0.1 pounds to about 10,000 pounds, in other embodiments, from about 1 pound to about 1,000 pounds, and in other embodiments, from about 10 pounds to about 1,000 pounds of the plant-based materials.

As suggested above, a suitable enzyme broth (i.e. enzyme broth 14) may be provided or produced, such as by fungal fermentation. The enzyme broth includes one or more enzymes capable of breaking down the cell walls in the physically-intact condition. This may be referred to as the one or more enzymes being capable of degrading all of the various types of cell wall carbohydrates. Enzyme broths produced by fungal fermentations may utilize soybean hulls as substrate and inducer.

The enzyme broth, which can also be referred to as the liquid enzyme medium, can include one or more enzymes and one or more liquid solvents. In one or more embodiments, the one or more enzymes can include cellulase (to hydrolyze cellulose), xylanase (to hydrolyze xylan and hemicellulose), and pectinase (to hydrolyze pectin). Other suitable enzymes include β-glucosidase, cellobiohydrolase, endoglucanase, polygalacturonase, pectin lyase, sucrose, α-galactosidase, and combinations thereof.

In one or more embodiments, the one or more enzymes can consist essentially of cellulase, xylanase, and pectinase, as these enzymes are believed to be particular useful for breaking down the cell walls in the physically-intact condition.

In one or more embodiments, the enzyme broth is devoid of or substantially devoid of protease, so that the enzyme broth does not break down the protein bodies from being intact protein bodies. These embodiments may also avoid destroying proteins that stabilize oil bodies in order to retain intact oil bodies. These embodiments may be quantified by the enzyme broth including less than 300 BAEE Units/mL protease, in other embodiments, less than 70 BAEE Units/mL protease, and in other embodiments, less than 20 BAEE Units/mL protease.

The values of BAEE Units/mL and protease assay may be determined by the Pierce Fluorescent Protease Assay Kit (Thermo Scientific, Number 23266/23267). An exemplary kit includes FTC-casein (κ-casein labeled with fluorescein isothiocyanate to yield the fluorescein thiocarbamoyl (FTC) derivative) and TPCK trypsin (trypsin treated with L-1-tosylamide-2-phenylethyl chloromethyl ketone (TPCK)). FTC-casein may be the protein substrate. TPCK trypsin may be the reference protease for comparison/calibration. FTC-casein (2.5 mg) may be dissolved in 500 μL ultrapure water to make a 5 g/L stock solution, 20 μL of which may be then mixed with 10 mL 0.05 M sodium citrate buffer (pH 4.8) to make the substrate solution for the assay. The substrate solution (50 μL) may be added with a 20 μL enzyme sample (or a TPCK trypsin standard) to a 96-well black plate (Greiner Bio One, Number 655076), mixed, and allowed to react at room temperature for 20 min. The reaction mixture may be next added with 200 μL 1 M Tris-HCl (pH 9.0), to provide the high pH required for emission of the fluorescein label. Fluorescence may be measured using a multimode microplate reader (Infinite 200 PRO, TECAN) at excitation and emission wavelengths of 485 and 538 nm, respectively. A calibration curve of fluorescence changes versus TPCK trypsin concentrations used (0-50 mg/L) may be generated by the same procedure. Accordingly, the fluorescence change generated by the enzyme sample can be converted to the equivalent TPCK trypsin concentration, and subsequently to BAEE U/mL by multiplying the factor of 16,273.

In one or more embodiments, the enzyme broth is devoid of or substantially devoid of oleosin-degrading enzymes that would otherwise break down the natural oleosins that surround and stabilize the oil bodies.

As suggested above, the presence or absence of a minor pretreating step (e.g. to remove hulls) may determine the most suitable composition of the enzyme broth. Also, the particularly utilized plant-based materials may also determine the most suitable composition of the enzyme broth.

The liquid solvent can be selected from the group consisting of water, sodium citrate buffer, sodium hydroxide, hydrochloric acid, citric acid, Ethylene diamine tetra-acetic acid (EDTA), ethanol, methanol, and combinations thereof. Suitable amounts of the solvent will be generally known to the skilled person. In one or more embodiments, a liquid solvent includes an organic solvent in an aqueous solution.

In one or more embodiments, the enzyme broth may be made from the fermentation of one or more fungus selected from the genera consisting of *Trichoderma, Aspergillus, Penicillium, Saccharomyces, Phanerochaete, Rhizopus, Fusarium, Neurospora, Podospora, Pichia*, and *Schizophyllum*. In one or more embodiments, the fungus is selected from the group consisting of *Trichoderma reesei* Rut-C30, *Aspergillus niger* NRRL 322, *Aspergillus niger* NRRL 325, *Aspergillus niger* NRRL 328, *Aspergillus niger* NRRL 334, *Aspergillus niger* NRRL 341, *Aspergillus niger* NRRL 348, *Aspergillus niger* NRRL 363, *Aspergillus niger* NRRL 566, *Aspergillus niger* NRRL 599, *Aspergillus niger* NRRL 2270, *Aspergillus niger* NRRL 13201, *Aspergillus niger* NRRL 13219, *Aspergillus niger* NRRL 62517 and *Aspergillus aculeatus* NRRL 2053, and combinations thereof.

As suggested above, the plant-based materials and enzyme broth are combined for enzymatic processing (i.e. enzymatic processing step 22). The enzymatic processing generally serves to hydrolyze the oligomeric and polymeric molecules of the cell walls into monomers. The particular conditions of the enzymatic processing, which will be further discussed herein below, may be adjusted based on the particular plant-based materials and/or enzyme broth utilized, and/or the desired products.

With respect to the enzymatic processing hydrolyzing the cell walls in the physically-intact condition, this may be quantified based on the amount of cell walls in the physically-intact condition that are sufficiently hydrolyzed during the enzymatic processing to become no longer physically-intact and thereby release protein bodies and oil bodies. In one or more embodiments, at least 50%, in other embodiments, at least 70%, in other embodiments, at least 80%, and in other embodiments, at least 85% of cell walls in the physically-intact condition are sufficiently hydrolyzed during the enzymatic processing. In one or more embodiments, at least 90%, in other embodiments, at least 95%, in other embodiments, at least 98%, in other embodiments, at least 99%, and in other embodiments, at least 99.5% of cell walls in the physically-intact condition are sufficiently hydrolyzed during the enzymatic processing. In one or more embodiments, about 98%, in other embodiments, about 99%, in other embodiments, about 99.5%, and in other embodiments, about 100% of cell walls in the physically-intact condition are sufficiently hydrolyzed during the enzymatic processing.

This may also be quantified based on the conversion of an amount of the total carbohydrates of the plant-based material into soluble carbohydrates. In one or more embodiments, at least 50%, in other embodiments, at least 70%, in other embodiments, at least 80%, and in other embodiments, at least 85% of the total carbohydrates of the plant-based material are converted into soluble carbohydrates during the enzymatic processing. In one or more embodiments, at least 90%, in other embodiments, at least 95%, in other embodiments, at least 98%, in other embodiments, at least 99%, and in other embodiments, at least 99.5% of the total carbohydrates of the plant-based material are converted into soluble carbohydrates during the enzymatic processing. In one or more embodiments, about 98%, in other embodiments, about 99%, in other embodiments, about 99.5%, and in other embodiments, about 100% of the total carbohydrates of the plant-based material are converted into soluble carbohydrates during the enzymatic processing.

This may also be quantified based on the total recovery of a particular product (e.g. intact oil bodies) with respect to the initial amount of the product component in the plant-based material. These values will be provided further herein with respect to product collection discussion.

The enzymatic processing, which may also be referred to as the hydrolysis step, may be characterized by enzyme concentration, which may also be referred to as enzyme loading. In one or more embodiments, the hydrolysis step is performed at an enzyme to plant-based material ratio of from about 0.5 mL/g to about 15 mL/g, in other embodiments, from about 1 mL/g to about 10 mL/g, and in other embodiments, from about 2 mL/g to about 8 mL/g. In one or more embodiments, the hydrolysis step is performed at an enzyme to plant-based material ratio of about 0.5 mL/g, in other embodiments, about 1 mL/g, in other embodiments, about 3 mL/g, in other embodiments, about 7 mL/g, and in other embodiments, about 10 mL/g. In one or more embodiments, the hydrolysis step is performed at an enzyme to plant-based material ratio of greater than 2 mL/g, in other embodiments, greater than 4 mL/g, and in other embodiments, greater than 8 mL/g.

The enzymatic processing may be characterized by protein concentration, which may also be referred to as substrate concentration or solid loading. In one or more embodiments, the hydrolysis step is performed at a solid loading of from about 25 g/L to about 450 g/L, in other embodiments, from about 40 g/L to about 200 g/L, and in other embodiments, from about 50 g/L to about 150 g/L. In one or more embodiments, the hydrolysis step is performed at a solid loading of about 50 g/L, in other embodiments, about 100 g/L, and in other embodiments, about 150 g/L.

The suitable enzyme activity or concentration generally depends on the particular plant-based material utilized (e.g. how much cellulose, pectin, and hemicellulose are in the plant-based material). In one or more embodiments, cellulase may be provided in the range of from about 3 to about 30 FPU (Filter Paper Unit) per g cellulose, pectinase may be provided in the range of from about 30 to about 400 U per g pectin, and xylanase may be provided in the range of from about 10 to about 200 U per g hemicellulose. The limiting enzyme activity (i.e. cellulase, pectinase, or xylanase) with respect to their corresponding carbohydrate polymers (i.e. cellulose, pectin, or hemicellulose) present in the particular plant material may also be used to determine a suitable concentration of enzymes in the enzyme broth.

In one or more embodiments, the hydrolysis step may be performed at a temperature of from about 30° C. to about 65° C., in other embodiments, from about 40° C. to about 60° C., and in other embodiments, about 45° C. to about 55° C.

In one or more embodiments, the hydrolysis step may be performed at a pH of from about 4.5 to about 6.0, in other embodiments, from about 4.7 to about 5.2, and in other embodiments, from about 4.8 to about 5.2. In one or more embodiments, the hydrolysis step is performed at a pH of about 4.7, in other embodiments, about 4.8, in other embodiments, about 5.1, and in other embodiments, about 5.2.

In one or more embodiments, the hydrolysis step is performed at a time of from about 2 hours to about 60 hours, in other embodiments, from about 6 hours to about 48 hours, and in other embodiments, from about 8 hours to about 24 hours.

In one or more embodiments, the hydrolysis mixture during the enzyme processing step may be subjected to sonication. Where sonication is utilized during hydrolysis mixture, the sonication may be pulsed ultrasound-mediated sonication. As suggested above, in some embodiments, sonication may also be applied before the enzyme processing, such that some embodiments include sonication before and during the enzyme processing.

In one or more embodiments, sonication during the enzyme processing step is performed at an interval time of from about 2 minutes to about 10 minutes per every about 1 hour to about 3 hours, in other embodiments, from about 1 minute to about 2 minutes per every about 1 hour to about 3 hours, and in other embodiments, from about 2 minutes to about 3 minutes per every about 1 hour to about 3 hours.

In one or more embodiments, sonication during the enzyme processing step may be performed at a power of from about 30 W to about 120 W, in other embodiments, from about 60 W to about 120 W, and in other embodiments, from about 30 W to about 60 W.

In one or more embodiments, sonication during the enzyme processing step may be performed at concentration of from about 0.5 W/mL to about 5 W/mL, in other embodiments, from about 0.75 W/mL to about 3.0 W/mL, and in other embodiments, from about 1 W/mL to about 2.5 W/mL.

As suggested above, following the enzymatic processing, the product may be separated (i.e. product separation step 24) into three main products. A first product (i.e. first product stream 26) generally includes the intact oil bodies as a primary component. A second product (i.e. second product stream 28) generally includes the hydrolyzed carbohydrates as a primary component. The carbohydrates may be characterized as soluble carbohydrates and insoluble carbohydrates, with respect to water. A third product (i.e. third product stream 30) generally includes the intact protein bodies as a primary component. As discussed below, each of the products may include a smaller amount of the non-primary components. That is, the third product that generally includes the intact protein bodies as a primary component may also include some intact oil bodies and some hydrolyzed carbohydrates. As suggested above, each of the three main products may undergo further processing for further concentration of the primary product component.

As suggested above, the product may be separated by a centrifuge in a centrifugation step. One skilled in the art will generally understand aspects of a desired separation, such as centrifugal force and time required, which may depend on the particular device utilized and the amount of material to be separated.

The first product including the intact oil bodies as a primary component may be collected from the top as a cream-like layer. This may be collected using a surface-layer skimming or suction mechanism. The second product including the hydrolyzed carbohydrates as a primary component may be collected from the middle section. The third product including the intact protein bodies as a primary component may be collected as a bottom layer. As suggested above, the collected products may undergo further processing for further desirability. The collected and/or further processed products may have a variety of applications, such as cosmetic, health-care, hygienic, and food.

As suggested above, in one or more embodiments, the various products can be collected without significant blending of the products that may otherwise destroy the structures of cells and subcellular protein and oil bodies, which if utilized would otherwise may separation more difficult.

The plant-based material includes an initial amount of intact oil bodies, carbohydrates, and intact protein bodies. The present method may be characterized by the amount of total recovery of each of these product components.

In one or more embodiments, the method provides a total recovery of intact oil bodies of greater than 40 wt. %, in other embodiments, greater than 60 wt. %, in other embodiments, greater than 80 wt. %, and in other embodiments, greater than 85 wt. %.

In one or more embodiments, the method provides a total recovery of carbohydrates of greater than 50 wt. %, in other embodiments, greater than 60 wt. %, and in other embodiments, greater than 80 wt. %.

In one or more embodiments, the method provides a total recovery of intact protein bodies of greater than 40 wt. %, in other embodiments, greater than 50 wt. %, and in other embodiments, greater than 60 wt. %.

In one or more embodiments, a first product generally including the intact oil bodies as a primary component includes greater than 50 wt. %, in other embodiments, greater than 60 wt. %, and in other embodiments, greater than 80 wt. %, in other embodiments, greater than 90 wt. %, and in other embodiments, about 95 wt. % of the initial intact oil bodies of the plant-based material. In one or more embodiments, a first product generally including the intact oil bodies as a primary component includes from about 50 to about 95 wt. %, in other embodiments, from about 60 to about 90 wt. %, in other embodiments, from about 80 to about 90 wt. %, of the initial intact oil bodies.

In one or more embodiments, a first product generally including the intact oil bodies as a primary component includes from about 3 wt. % to about 15 wt. %, in other embodiments, from about 5 wt. % to about 15 wt. %, and in other embodiments, from about 5 wt. % to about 10 wt. %, of the initial carbohydrates of the plant-based material.

In one or more embodiments, a first product generally including the intact oil bodies as a primary component includes from about 5 to about 20 wt. %, in other embodiments, from about 10 to about 15 wt. %, and in other embodiments, from about 10 to about 12 wt. %, of the initial intact protein bodies.

In one or more embodiments, a second product generally including the hydrolyzed carbohydrates as a primary component includes greater than 50 wt. %, in other embodiments, greater than 60 wt. %, and in other embodiments, greater than 70 wt. %, in other embodiments, greater than 75 wt. %, and in other embodiments, about 80 wt. % of the initial carbohydrates of the plant-based material. In one or more embodiments, a second product generally including the hydrolyzed carbohydrates as a primary component includes from about 50 to about 85 wt. %, in other embodiments, from about 60 to about 80 wt. %, in other embodiments, from about 70 to about 80 wt. %, of the initial carbohydrates.

In one or more embodiments, a second product generally including the hydrolyzed carbohydrates as a primary component includes less than 5 wt. %, in other embodiments, less than 3 wt. %, in other embodiments, from about 1 to about 3 wt. %, of the initial intact oil bodies.

In one or more embodiments, a second product generally including the hydrolyzed carbohydrates as a primary component includes from about 25 to about 40 wt. %, in other embodiments, from about 30 to about 40 wt. %, in other embodiments, from about 25 to about 35 wt. %, of the initial intact protein bodies.

In one or more embodiments, a third product generally including the intact protein bodies as a primary component includes greater than 40 wt. %, in other embodiments, greater than 50 wt. %, in other embodiments, greater than 55 wt. %, and in other embodiments, greater than 60 wt. % of the initial intact protein bodies. In one or more embodiments, a third product generally including the intact protein bodies as a primary component includes from about 40 to about 65 wt. %, in other embodiments, from about 40 to about 55 wt. %, in other embodiments, from about 45 to about 55 wt. %, of the initial intact protein bodies.

In one or more embodiments, a third product generally including the intact protein bodies as a primary component includes from about 5 to about 15 wt. %, in other embodiments, from about 2 to about 10 wt. %, in other embodiments, from about 1 to about 5 wt. %, of the initial intact oil bodies.

In one or more embodiments, a third product generally including the intact protein bodies as a primary component includes from about 10 to about 30 wt. %, in other embodiments, from about 10 to about 25 wt. %, in other embodiments, from about 15 to about 20 wt. %, of the initial carbohydrates.

In addition to the advantages discussed above, the present method may offer one or more other advantages: the method may be devoid or substantially devoid of hexane; the method may be devoid of a hexane extraction step; the method may be devoid of a flaking step; the method may be devoid of an extrusion step; the method may be devoid of a grinding step; the method may be devoid of a crushing step; the method may be devoid of a pressing step; the method may be devoid of a funnel separation step; and/or the method may be devoid of an acid precipitation step.

In one or more embodiments, method 10 may be continuous. In other embodiments, method 10 may be semi-continuous.

In light of the foregoing, it should be appreciated that the present invention significantly advances the art by providing an improved method of enzyme-based processing of plant-based materials. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof.

Materials & Equipment

Full-fatted, dehulled, cracked soybeans were provided by Archer Daniels Midland (Decatur, Ill.). $(NH_4)_2SO_4$ (granular), $KH_2PO_4$ (99% purity), HCl (concentrated, 37.4%) and NaOH (98.8%) were purchased from Fisher Scientific (Waltham, Mass.). Proteose peptone (from meat, Type I, for microbiology), $MgSO4.7H2O$ (99%), $MnSO_4.4H_2O$ (99%), $ZnSO_4.7H_2O$ (ACS reagent grade), $CoCl_2.6H_2O$, $FeSO_4.7H_2O$ (reagent grade), $CaCl_2.2H_2O$ (reagent grade), urea (98%), $NaN_3$ (>99%) and dinitrosalicylic acid (DNS, 98%) were purchased from Sigma-Aldrich (St. Louis, Mo.). The *Aspergillus niger* (NRRL 341) seed culture was obtained from the United States Department of Agriculture (USDA) Agricultural Research Service (ARS) Culture Collection (Peoria, Ill.). Two 3-L Bioflo 110 fermentors (New Brunswick Scientific; Edison, N.J.) were used for enzyme production by fermentation. Absorbance was measured using a spectrophotometer (UV-1601, Shimadzu; Columbia, Md.). Hydrolysis experiments were conducted in a shaker (Thermo Scientific MaxQ 5000 Incubating/Refrigerating floor shaker; Ashville, N.C.). Two centrifuges were used: a Sorvall Legend X1R centrifuge (Thermo Scientific; Waltham, Mass.) and a Sorvall RC 5C centrifuge (DuPont; Wilmington, Del.). The vacuum oven used was manufactured by Lab-line Instruments (Melrose Park, Ill.).

Enzyme Production

Enzyme was produced by *A. niger* fermentation in the 3-L fermentor containing 1 L medium of the following composition: soybean hulls, 40 g/L; proteose peptone, 1.4 g/L; $(NH_4)2SO_4$, 4 g/L; $K_2HPO_4$, 0.32 g/L; $KH_2PO_4$, 0.21 g/L; and $MgSO_4.7H_2O$, 1 g/L. Inoculation with a pre-grown culture gave an initial cell concentration of about 0.1 g/L. Temperature and agitation were maintained at 23° C. and 350 rpm. Dissolved oxygen concentration (DO) dropped along cell growth and was maintained at 20% by supplementation of pure oxygen. pH was 6.7 initially and was programmed (with controlled addition of 1 M NaOH or HCl) to drop linearly to 6.0 in the first 3 days, maintain at 6.0±0.1 in the 4th day, and then drop linearly again to 5.0 at the end of the 5th day when the fermentation was stopped. The fermentation broth was centrifuged at 9,000 g for 10 min (Sorvall RC 5C) and the supernatant collected was used as enzyme broth in the hydrolysis. The enzyme broth was measured to have the following activities: 0.62 FPU (Filter Paper Unit)/mL cellulase, 93 U/mL xylanase, 5.8 U/mL pectinase, 6.4 U/mL α-galactosidase and 65.3 N-benzoyl-L-arginine ethyl ester (BAEE) U/mL protease. For all activities, one unit (U) is the enzyme amount that catalyzes the hydrolysis of substrate to produce 1 μmol of monomeric product per min. The substrates used in the analyses were: Whatman No. 1 filter paper for cellulase, beech-wood xylan for xylanase, citrus pectin for pectinase, and p-nitrophenyl-α-D-galactopyranoside for α-galactosidase. The monomeric products detected were: glucose for cellulase, xylose for xylanase, galacturonic acid for pectinase, and p-nitrophenol for α-galactosidase. The protein content in the fermentation broth was measured to be 0.11 g/L.

Particle Size Screening

To quantitate the particle size effect, cracked soybeans were sieved (mesh No. 8, 16 and 40) to collect particles in 4 size groups, designated large (L), medium (M), small (S), and extra small (XS) with the following sizes: L, ≥2.38 mm; M, 1.19-2.38 mm; S, 0.42-1.19 mm; and XS, <0.42 mm.

Hydrolysis Conditions

The enzyme processing was conducted in 250 mL shake flasks with 250 rpm rotation in an orbital shaker with 4 g soybean particles and 40 mL liquid, i.e. at 100 g/L solid loading, at 50° C. temperature and pH 4.8 for 24 hours. These hydrolysis conditions were used in all of the below examples, unless specified otherwise.

Without Sonication

For hydrolysis experiments without sonication, 40 mL undiluted enzyme broth was used (i.e., at enzyme loading of 10 mL per g soybean), except for studying of enzyme loading effect. In the latter discussion, 4 enzyme loading levels were investigated: 1, 2, 4 and 10 mL/g. This also included a system where the 2 mL/g enzyme loading was supplemented with 10 FPU/g commercial cellulase and 30 U/g commercial pectinase. The commercial Spezyme CP (DuPont; Cedar Rapids, Iowa) had 147 FPU/mL cellulase and the commercial pectinase (Sigma-Aldrich; St. Louis, Mo.) had 121 U/mg pectinase activity.

With Sonication

For the ultrasound-mediated enzyme processing experiments, two levels of enzyme loading were used: 2 and 10 mL/g, added in one initial batch or in two fed-batch steps (0 and 6 h into enzyme processing). A Misonix Ultrasonic Processor (model XL2020; Misonix Inc., Farmingdale, N.Y.) was used for sonication. The ultrasonic probe was placed at the center of the flask containing hydrolysis mixture. Mixing was enhanced by magnetic stirring. The flask was exposed to room temperature during the sonication. The sonication effect was investigated in two sets of experiments. First, sonication was applied only to an aqueous suspension of cracked soybeans (S-sized, 0.42-1.19 mm) before the enzyme was added. In these experiments, the aqueous suspensions were sonicated for 5 min at different power levels, from 30 to 120 W (corresponding to 0.75 to 3.0 W/mL), and then added with enzyme broth to initiate the enzyme processing. Pulsed ultrasound-mediated enzyme processing was evaluated in the second set of experiments where sonication was applied before and during the enzyme processing. The ultrasound treatment was applied with 60 W power (i.e., 1.5 W/mL) every 3 h for 10 min during the first 12 h of enzyme processing and then once at the end (24 h).

Separation and Collection of Products

After the enzyme processing, the mixture was centrifuged for 10 min at 13,000×g. Oil bodies floated to the top as a cream-like layer, which was collected carefully using a pipette. The middle section was the liquid containing mainly hydrolyzed carbohydrates. Settled at the bottom was the insoluble solid containing majority of the protein. These three portions were separately analyzed for oil, protein, and carbohydrate contents as described herein. The oil bodies collected by centrifugation were also observed by using an Olympus light microscope coupled to a DP71 digital camera.

Visualization by Confocal Laser Scanning Microscopy (CLSM)

An Olympus FV1000 confocal laser scanning microscope (CLSM) (Olympus America Inc., Center Valley, Pa.) was used. Three fluorochromes were selected to stain the samples: acridine orange and rhodamine B for protein and Nile blue for oil bodies. One drop of a dye stock solution (1% w/v in water) was added to a 2-2.5 mL sample and mixed well before slide preparation. The CLSM was equipped with three lasers for excitation; an argon laser ($\lambda_{excitation}$ 488 nm), a diode pumped solid-state laser ($\lambda_{excitation}$ 561 nm) and a helium-neon laser ($\lambda_{excitation}$ 633 nm). The micrographs obtained with samples stained by rhodamine B did not provide additional information; therefore, only those by the other two dyes are described in the Results and Discussion section. CLSM observations were made on the samples incubated with deionized water without enzyme and the samples taken along the enzyme processing. The sample was added with the dye solution and mixed gently. The stained sample was placed on the CLSM plate and added with one drop of glycerol to reduce drying during the scanning. CLSM observations confirmed the enzymatic destruction of cell walls.

Analytical Methods

Carbohydrate Analysis

Hydrolyzed carbohydrate concentrations in samples were measured in terms of total carbohydrate concentrations by the phenol-sulfuric acid method and the reducing sugar concentrations by the dinitrosalicylic (DNS) acid method. Briefly, for the phenol-sulfuric acid method, 1 mL sample was mixed with 1 mL aqueous phenol solution (5% w/w) in a test tube, followed by addition of 5 mL concentrated sulfuric acid. The phenol solution was freshly prepared before each batch of analysis. After 10 min reaction without mixing, the mixture was vortexed for 30 s, cooled to room temperature, and then measured for the absorbance at 490 nm. The total carbohydrate concentration was obtained using a calibration curve generated using glucose as standard. For the reducing sugar analysis by the DNS method, the reagent contained 10 g/L 3,5-dinitrosalicylic acid, 16 g/L NaOH and 300 g/L sodium potassium tartrate (Rochelle salt). 3 mL DNS reagent and 1 mL supernatant sample were mixed in a test tube and then heated in a boiling water bath for 5 min. Deionized water was added to stop the reaction and give a total volume of 25 mL in the tube. After being cooled to the ambient temperature, the reacted mixture was measured for the absorbance at 550 nm. Monomeric sugars were measured using a high performance liquid chromatography (HPLC) system (Shimadzu LC 10A) with a refractive index detector (RID-10A). A carbohydrate column (Supelcogel Pb, 30 cm×7.8 mm) with a guard column (No. 59345, 50 mm×4.6 mm) was used at 80° C. for monosaccharides analysis. The mobile phase was HPLC grade water at a flowrate of 0.5 mL/min. For galacturonic acid measurement, an ion exchange column, Aminex HPX-87H (Bio-Rad, Hercules, Calif.) was used at 35° C., with 0.6 mL/min 0.005 N $H_2SO_4$ as the mobile phase. Calibration curves for converting the peak areas to concentrations were established with standard solutions of pure monomeric sugars.

Protein Content Measurement

The Kjeldahl method was used to measure the nitrogen contents of both liquid and solid samples. The nitrogen content was multiplied by 6.25 to estimate the protein content. A 50 mL sample containing 10 to 200 mg/L protein was added to a flask and digested with 10 mL reagent that contained 134 ml/L concentrated $H_2SO_4$, 134 g/L $K_2SO_4$ and 7.3 g/L $CuSO_4$. The digestion was carried out to completion, until the reaction mixture became a clear solution. Then 30 mL water and 10 mL of a distillation reagent containing 500 g/L NaOH and 25 g/L $Na_2S_2O_3.5H_2O$ were added to the digested sample. This mixture was distilled (RapidStill 1, Labconco, Kansas City, Mo.) to produce ammonia gas, which was absorbed in 0.1 N $H_3BO_3$. Then the $H_3BO_3$ solution was titrated using 0.1 N $H_2SO_4$ to determine the nitrogen concentration in the sample.

Oil Analysis

The total oil content was determined by expressing total lipids as fatty acid methyl esters (FAME). The procedure was based on transesterification of lipids to FAME. 5 to 10 mg samples were pre-weighed in the gas chromatography (GC) vials. Samples were then dried in a desiccator under vacuum overnight. 25 µl of a prepared C13:0 FAME internal standard (10 g/L), 200 µl of a chloroform-methanol mixture (2:1, v/v) and 300 µl of a 0.6 M HCl in methanol were added to each sample vial. The vial was immediately sealed and heated at 85° C. for 1 h in a pre-heated block. The sample was cooled to room temperature and then added with 1 mL HPLC grade hexane. After being vortexed for mixing, the sample was left undisturbed for phase separation. The upper phase was then withdrawn and injected for GC analysis (Model GC-17A, Shimadzu Corporation, Kyoto, Japan). The FAME chromatogram was obtained and converted to the total oil concentration according to the calibration chromatogram generated using a known standard FAME mixture (F.A.M.E. Mix, C4-C24, 18919, Sigma Aldrich, St. Louis, Mo.).

Results

Enzymatic Separation of Soybean Components

CLSM micrographs were obtained with cracked soybean particles dispersed in water (no enzyme) for 1 h in the orbital shaker. The samples shown were stained with acridine orange. Cotyledon cells containing intracellular materials could be seen. Intact cell wall structures were clear. Protein bodies (PBs) and oil bodies (OBs) that make up the intracellular materials were clearly shown, where protein bodies were in darker color and the surrounding bright green color was from the oil bodies. Some of the cells were found empty without intracellular materials, presumably because the shaking movements dislodged the intracellular materials from some of the cells. The protein and oil bodies inside the inner layers of cells were not be emptied because they were enclosed by intact cell walls.

Two CLSM micrographs were obtained for samples of cracked soybeans that have been subjected to 6 h enzyme processing without sonication. The enzyme processing was done at pH 4.8 and 50° C. with 4 mL/g enzyme loading and 100 g/L solid loading. A sample was stained with acridine orange and a sample was stained with both Nile blue and acridine orange. Nile blue stains the lipid particles specifically, rendering them in yellow to red color. The micrographs showed that cell walls were removed by the enzyme. Some of the oil bodies (in yellow color) were also still associated with the protein body aggregates while some other oil bodies (in red color) appeared to be more separated from the protein bodies and formed their own agglomeration.

Two CLSM micrographs and an optical image were obtained from samples of cracked soybeans that have been subjected to 6-h enzyme processing followed by 10-min 60-W sonication. The enzyme processing was done at pH 4.8 and 50° C. with 4 mL/g enzyme loading and 100 g/L solid loading. Protein bodies (in green color) were found very well dispersed. The dispersion observed in this sample area was surprisingly uniform, presumably still attached to some unseen structures underneath this layer. Some oil bodies, much smaller in size, were also seen in yellow, brown, or red color. Some oil bodies were attached with the protein bodies; others appeared to be separated. The roughly cylindrical shapes of the intracellular materials originally present in the cells were no longer maintained. Protein bodies appeared to be more randomly aggregated. More importantly, no yellow or red colored oil bodies were seen here. This suggests that oil bodies were separated from these protein bodies due to the sonication.

The CLSM and optical microscopic observations clearly showed that the A. niger enzyme used effectively removed the cell wall structures surrounding the protein bodies and oil bodies. Separation of oil bodies from the protein bodies can be enhanced by sonication. The separated oil bodies and protein bodies can be collected by centrifugation as described herein. Conceptually, the enzyme is believed to have destroyed cell walls in an inward layer-by-layer manner.

Particle Size

With respect to the particle size analysis suggested above and respective examples thereof, the oil, carbohydrate and protein recoveries were obtained in individual portions, i.e., the top cream layer of oil body suspension, middle layer of aqueous hydrolysate, and the bottom layer of protein concentrate, after 24 h processing with 10 ml/g enzyme. For all of the samples measured, the total carbohydrate concentrations and reducing sugar concentrations were found to be very close, which suggested that the hydrolyzed carbohydrates were predominantly monomerized. Otherwise, the total carbohydrate concentration measured would be clearly higher than the reducing sugar concentration. The essentially complete carbohydrate monomerization was confirmed by the HPLC analysis which detected no remaining oligosaccharides.

Particle size affected the recoveries of oil body, protein, and hydrolyzed carbohydrates. As the particle size decreased from L to XS, more carbohydrate became solubilized in the hydrolysate. For example, with the XS particle size, about 77% carbohydrate was collected in the hydrolysate and 14% remained with the solids. Note however that some of the 14% carbohydrate was soluble but trapped with the hydrolysate as part of the wet soy protein concentrate collected by centrifugation. With decreasing particle sizes, the higher cell wall carbohydrate hydrolysis also led to release of more oil bodies into the top cream layer; oil recovery in this layer increased from 69% with L-sized particles to 90% with the XS-sized particles. The higher cell wall hydrolysis of smaller particles would also free more protein bodies from confinement in cell structures. This effect was however associated with lower protein recovery in the protein precipitate (decreasing from 55% for L-sized particles to 46% for XS-sized particles) and more protein in the hydrolysate and oil bodies/cream layers. This observation is believed to be at least partially attributable to the presence of N-containing substances (measured to represent protein) that, once freed from cell wall confinement/association, are naturally soluble at the hydrolysis pH 4.8; even among proteins, some have different pI and not all would precipitate completely at pH 4.8. The protease activity in the A. niger enzyme, although from a selected strain and designed fermentation for low protease production, likely also contributed to the higher proteinaceous content in hydrolysate when more protein bodies were released from smaller particles.

Enzyme Loading

Figure 3:
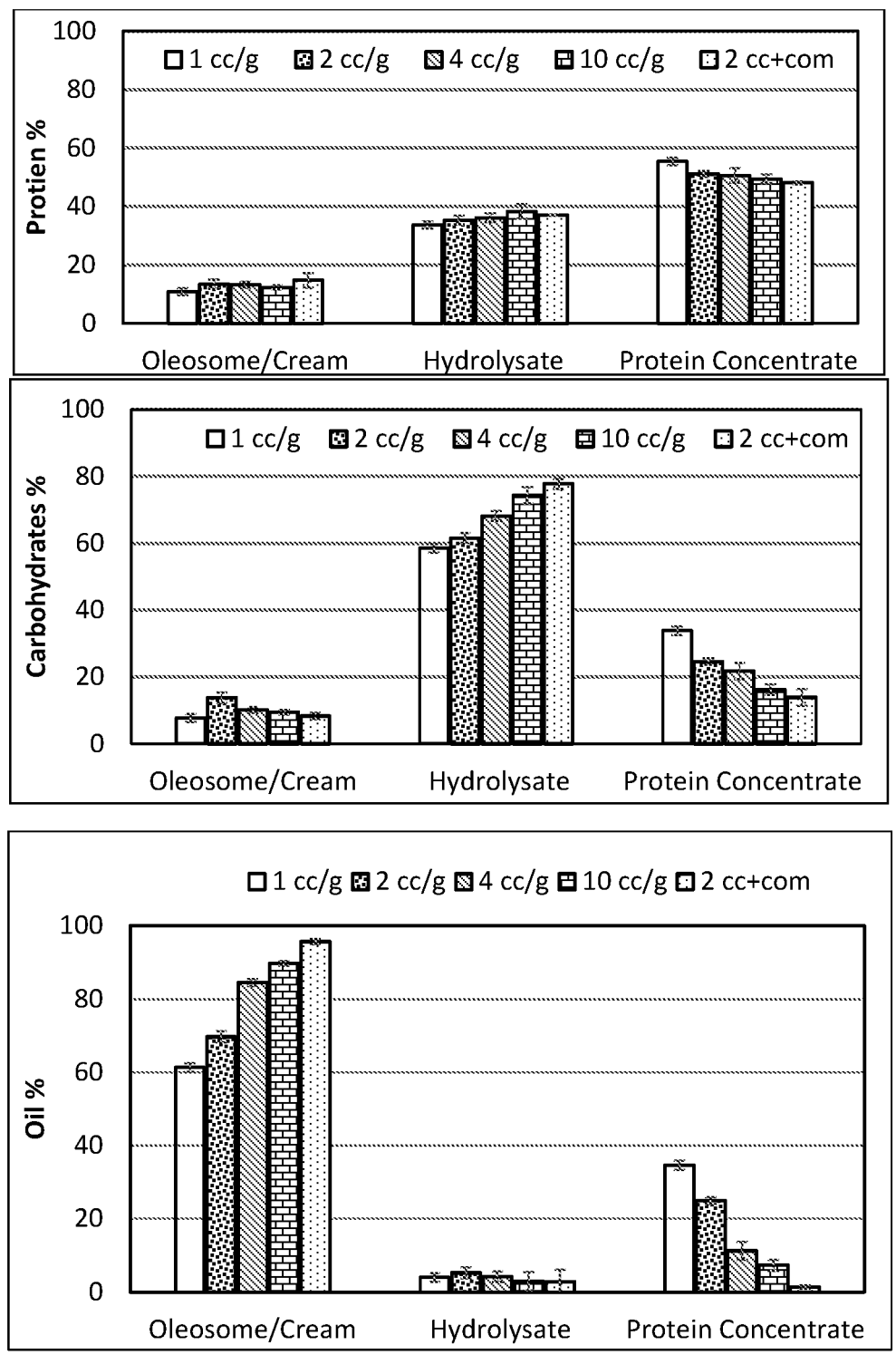
FIG. 3 is graphs showing the effect of enzyme loading on oil extraction and protein-carbohydrate separation according to examples of one or more embodiments of the present invention.

S-sized cracked soybeans were processed by the enzyme broth at different enzyme loadings: 1, 2, 4 and 10 mL per g beans, and also by 2 mL/g enzyme plus commercial cellulase and pectinase. The results of protein, carbohydrate, and oil recoveries in different layers are summarized in FIG. 3. Qualitatively, increasing enzyme loading had similar effects as decreasing particle size. As the enzyme loading was decreased from 10 mL/g to 1 mL/g, the oil extraction (in oil bodies/cream layer) decreased from 90% to 60% and the carbohydrate recovery (in hydrolysate) decreased from 74% to 58%. The system with 2 mL/g enzyme broth plus commercial cellulase and pectinase gave even more pronounced effects than the highest enzyme broth loading of 10 mL/g. For comparison, the 10 mL/g enzyme broth had, per g soybeans, 6.2 FPU cellulase, 930 U xylanase, 58 U pectinase and 64 U α-galactosidase while the commercial enzymes-supplemented 2 mL/g enzyme broth system had 11.2 FPU cellulase, 186 U xylanase, 42 U pectinase and 13 U α-galactosidase. So, the supplemented system had almost 2-fold higher cellulase activity, about 30% lower pectinase activity, and much lower xylanase and α-galactosidase activities. The positive effect of the higher cellulase activity appeared to surpass the negative effects of lower pectinase, α-galactosidase and xylanase activities, giving the net effects of enhanced cell wall destruction and carbohydrate solubilization as well as higher collection of oil in the top cream layer.

The available xylanase and pectinase were much higher even after reductions in the commercial enzymes-supplemented system, i.e., 186 U/g xylanase and 42 U/g pectinase. It is therefore reasonable to find the dominantly positive effect due to the raised cellulase activity in the commercial enzymes-supplemented system. The finding indicates the value of increasing cellulase activity in the enzyme, if to improve processing efficiency particularly for using relatively large soybean particles in the process.

Sonication Prior to Enzyme Processing

Figure 4:
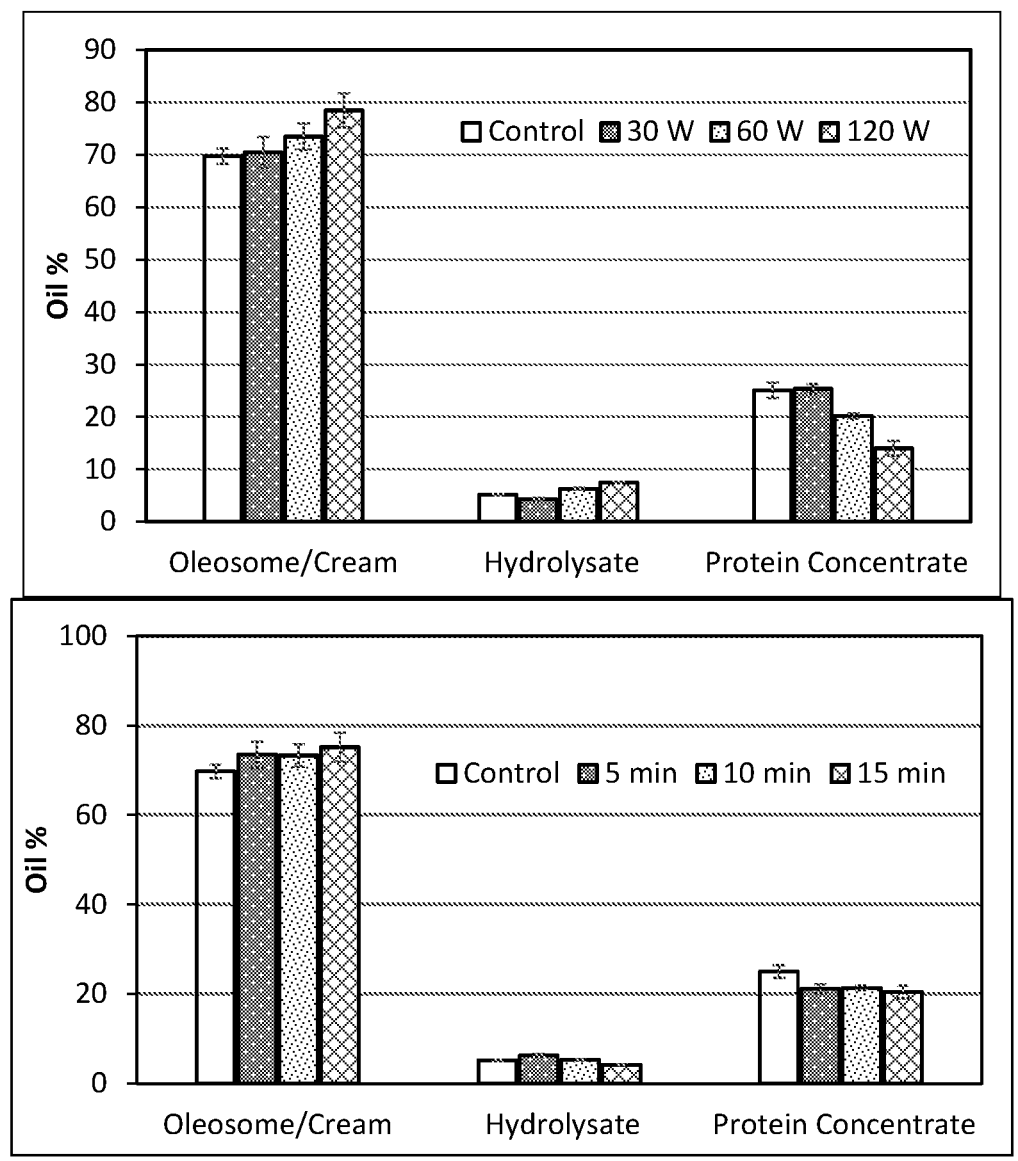
FIG. 4 is graphs showing the effect of ultrasound power and time in terms of oil recoveries in the top oil/oleosome phase, middle hydrolysate phase, and bottom protein concentrate phase according to examples of one or more embodiments of the present invention.

Results of oil recovery in the oil bodies/cream layer are shown in FIG. 4 for the effect of ultrasound power applied for 5 min to S-sized cracked soybean particles before the enzyme broth (2 mL/g) was added to initiate the hydrolysis. Sonication improved the oil recovery, from 70% to 78% (p=0.02) at the highest ultrasound power (120 W). However, with this high ultrasound power, some oil bodies were broken as seen in CLSM micrographs. Damages to oil bodies were not apparent at 30 W and 60 W ultrasound power where oil bodies remained as individual bright green entities. On the other hand, after sonication at 120 W, oil from the broken oil bodies coalesced into large bright green areas.

The effect on oil recovery by different sonication durations (5 to 15 min) at 30 W power level is also shown in FIG. 4. The 5-min sonication improved the oil recovery over that in the enzyme processing without any sonication (p=0.038) but further increases in sonication duration did not have a significant effect in giving even higher oil recoveries (p=0.127). It is thought that sonication prior to the enzyme processing may improve the process performance mainly by dislodging or loosening up the protein bodies and oil bodies in outermost layer of cells with cell walls already broken by an earlier bean cracking process. While this effect can expose more cell wall for ready hydrolysis initially, the sonication may not significantly affect the subsequent hydrolysis of the intact cell walls of inner cells.

Pulsed Ultrasound-Mediated Enzyme Processing

Sonication prior to the enzyme processing was believed to offer improvement by loosening up the outermost layer of exposed cells in the cracked soybeans. It was not believed to affect the inner cells still with intact cell walls. Pulsed ultrasound-mediated enzyme processing was designed where sonication was applied before and during the enzyme processing.

Figure 5:
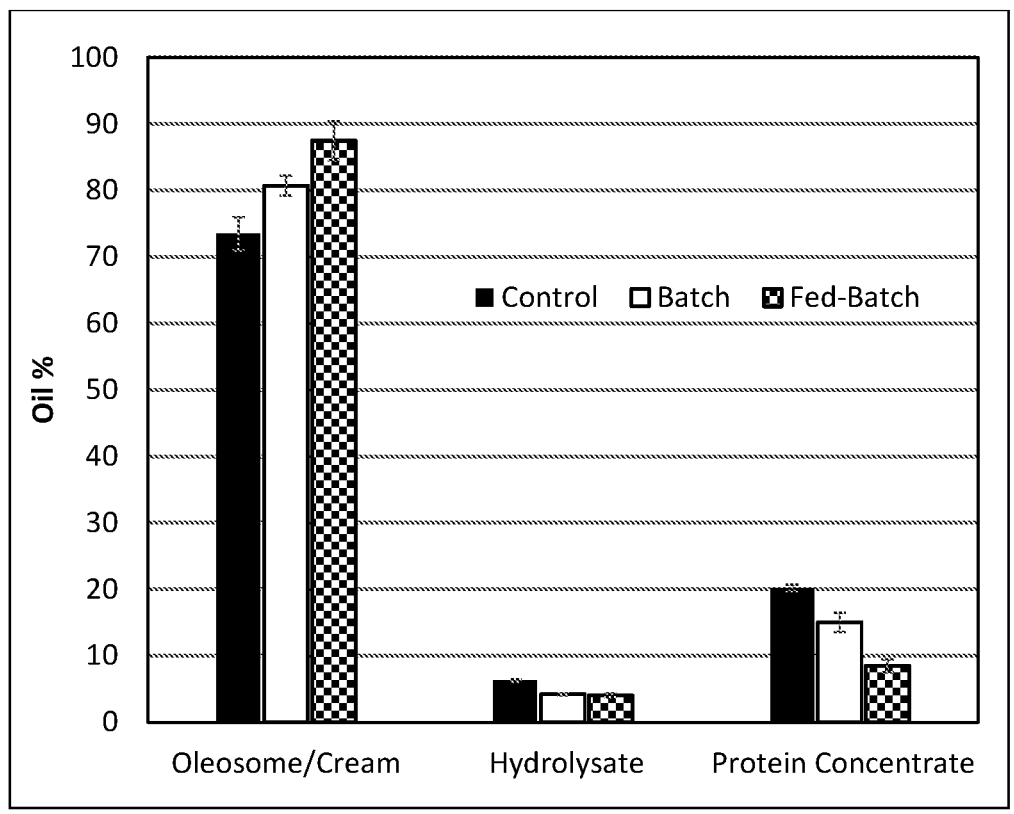
FIG. 5 is a graph showing the effect of pulsed ultrasound-mediated enzyme processing in terms of oil recoveries in the top oil/oleosome phase, middle hydrolysate phase, and bottom protein concentrate phase according to examples of one or more embodiments of the present invention.

Sonication was applied at a 60 W power level. To the "Control" system, 10 min sonication was applied only before the enzyme processing. To the "Batch" and "Fed-Batch" systems, 10 min sonication was applied before and during the enzyme processing every 3 h in the first 12 h of enzyme processing and then once at the end (24 h). The "Control" and "Batch" systems had the entire enzyme (2 mL/g) added at the beginning of enzyme processing; the "Fed-Batch" systems had half of the 2 or 10 mL/g enzyme added at the beginning and the remaining half added after 6 h into the enzyme processing. The Fed-Batch system was included to minimize the potential effect of enzyme denaturation by sonication. Results were summarized for the oil, protein, and carbohydrate recoveries (or % distributions) in each collected layer (i.e., top oil bodies/cream layer, middle hydrolysate layer, and bottom protein concentrate layer) and for the composition of each layer in wt. % of oil, protein and carbohydrate. The oil recoveries are shown in FIG. 5.

The pulsed sonication during enzyme processing was more effective than the control with sonication only before the enzyme processing. At the same enzyme loading of 2 mL/g, the pulsed sonication improved the oil recovery in the oil bodies/cream layer from 70% (control) to 81% in the "Batch" system and to 87% in the "Fed-Batch" system. Estimated by linear interpolation of the oil recovery results obtained with different enzyme loadings without sonication, reaching 81% and 87% recoveries would require about 3.5 ml/g and 7.4 ml/g enzyme loading, respectively. Accordingly, the oil recoveries improved by the pulsed sonication were equivalent to about 43% and 73% saving in enzyme loading in the Batch and Fed-Batch enzyme addition systems, respectively. The fatty acid composition of oil collected in the cream layer was measured. Pulsed ultrasonic treatment also improved the carbohydrate recovery in the hydrolysate from 62% in the control to 78% in the fed-batch system, compared at the same 2 mL/g enzyme. These improvements may be attributed to sonication-enhanced dislodging of oil and protein bodies from remaining soybean particles, which helped expose cell wall for hydrolysis, and to better separation of oil bodies from the dislodged oil-protein mixture. The latter separation increased the oil content in the top cream layer from 59% in the control to 82% in the fed-batch system with the same 2 mL/g enzyme, and, correspondingly, increased the protein content in the bottom protein concentrate layer from 67% in the control to 77% in the fed-batch system, compared favorably to the 65-67% protein in commercial SPCs. The protein content can be raised further because 17% of the SPC was carbohydrate which included mostly soluble monomers in the hydrolysate trapped in the wet mass collected by centrifugation. A wash step could remove soluble carbohydrates and increase the protein content of washed SPC, possibly to >90% for SPI grade products.

The hydrolysate collected from the pulsed ultrasonication-treated fed-batch system with 2 mL/g enzyme had 61% carbohydrate and 36% protein. The carbohydrate was essentially all monosaccharides. This hydrolysate stream can be used directly as a protein-rich fermentation substrate to produce value-added bioproducts (e.g., arabitol). The proteinaceous substances in hydrolysate was found as an excellent nitrogen source for yeast growth in the arabitol production process, without requirement of any additional nitrogen source.

In the pulsed sonication-treated fed-batch system with the higher 10 mL/g enzyme loading, the oil recovery reached 95% in the top cream layer with 86% oil content; the carbohydrate recovery was 82% in the hydrolysate layer with 64% carbohydrate content; and the protein recovery was 63% in the SPC layer with 82% protein content.

What is claimed is:

1. A method of enzyme-based processing of plant-based materials, the method comprising steps of:
   providing a bulk amount of a plant-based material, the bulk amount of the plant-based material including a plurality of individual plant-based materials having cell walls, wherein the bulk amount of the plant-based material includes at least 90% of the cell walls in a physically-intact condition relative to a naturally-occurring amount of the cell walls in the physically-intact condition, wherein the physically-intact condition is defined as having unbroken cell walls;
   providing an enzyme broth having an enzyme capable of breaking down the cell walls in the physically-intact condition;
   combining the bulk amount of the plant-based material with the enzyme broth;
   allowing the enzyme capable of breaking down the cell walls in the physically-intact condition to break down at least a portion of the cell walls in the physically-intact condition to thereby produce intact oil bodies, hydrolyzed carbohydrates, and intact protein bodies;
   collecting a first product stream including the intact oil bodies;
   collecting a second product stream including the hydrolyzed carbohydrates; and
   collecting a third product stream including the intact protein bodies, wherein the third product stream is a solid product.

2. The method of claim 1, wherein the bulk amount of the plant-based material includes at least 95% of the cell walls in the physically-intact condition relative to the naturally-occurring amount of the cell walls in the physically-intact condition.

3. The method of claim 1, wherein the first product stream includes at least 50 wt. % of the intact oil bodies, wherein the second product stream includes at least 50 wt. % of the hydrolyzed carbohydrates, and wherein the third product stream includes at least 40 wt. % of the intact protein bodies.

4. The method of claim 1, wherein the enzyme capable of breaking down the cell walls in the physically-intact condition comprises cellulase, xylanase, and pectinase.

5. The method of claim 1, wherein the plant-based material has an average particle size from about 2.38 mm to about 1.19 mm.

6. The method of claim 1, wherein the plant-based material has an average particle size from about 1.19 mm to about 0.42 mm.

7. The method of claim 1, wherein the bulk amount of the plant-based material includes about 100% of the cell walls in the physically-intact condition relative to the naturally-occurring amount of the cell walls in the physically-intact condition.

8. A method of enzyme-based processing of plant-based materials, the method comprising steps of:
- providing a bulk amount of a plant-based material, the bulk amount of the plant-based material including a plurality of individual plant-based materials having cell walls, wherein the bulk amount of the plant-based material includes at least 90% of the cell walls in a physically-intact condition relative to a naturally-occurring amount of the cell walls in the physically-intact condition, where the physically-intact condition is defined as having unbroken cell walls;
- providing an enzyme broth having an enzyme capable of breaking down the cell walls in the physically-intact condition;
- combining the bulk amount of the plant-based material with the enzyme broth;
- allowing the enzyme capable of breaking down the cell walls in the physically-intact condition to break down at least a portion of the cell walls in the physically-intact condition to thereby produce intact oil bodies, hydrolyzed carbohydrates, and intact protein bodies;
- collecting a first product stream including the intact oil bodies;
- collecting a second product stream including the hydrolyzed carbohydrates; and
- collecting a third product stream including the intact protein bodies;

wherein the method further comprises a step of sonicating the plant-based material before the step of allowing.

9. The method of claim 8, wherein the method further comprises a step of sonicating during the step of allowing.

10. The method of claim 1, wherein the bulk amount of the plant-based material includes a total amount of intact oil bodies, wherein the step of collecting the first product stream includes collecting at least 40 wt. % of the total amount of intact oil bodies.

11. The method of claim 1, wherein the bulk amount of the plant-based material includes a total amount of carbohydrates, wherein the step of collecting the second product stream includes collecting at least 50 wt. % of the total amount of carbohydrates as hydrolyzed carbohydrates.

12. The method of claim 1, wherein the amount of the plant-based material includes a total amount of intact protein bodies, wherein the step of collecting the third product stream includes collecting at least 40 wt. % of the total amount of intact protein bodies.

13. The method of claim 1, wherein the method further comprises a step of sonicating the plant-based material before the step of allowing.

14. The method of claim 8, wherein the third product stream is a solid product.

* * * * *